United States Patent [19]

Masuda et al.

[11] Patent Number: 4,474,811

[45] Date of Patent: Oct. 2, 1984

[54] ANTI-INFLAMMATORY OPHTHALMIC SOLUTION AND PROCESS FOR PREPARING THE SAME

[75] Inventors: Kiyoshi Masuda, Otsu; Takashi Ikari, Shiga; Takashi Matsuyama, Shiga; Akio Terashima, Shiga; Takao Goto, Kusatsu, all of Japan

[73] Assignee: Kakenyaku Kako Co., Ltd., Tokyo, Japan

[21] Appl. No.: 411,028

[22] Filed: Aug. 24, 1982

[30] Foreign Application Priority Data

Dec. 24, 1981 [JP] Japan .............................. 56-214189

[51] Int. Cl.³ ................... A61K 31/19; A61K 47/00
[52] U.S. Cl. ........................................ 424/317; 424/361
[58] Field of Search ................. 424/317, 361; 562/492

[56] References Cited

U.S. PATENT DOCUMENTS

| | | | |
|---|---|---|---|
| 3,932,499 | 1/1976 | Adams et al. | 562/492 |
| 4,202,988 | 5/1980 | Wissner et al. | 424/317 |
| 4,263,457 | 4/1981 | Takeda et al. | 562/492 |
| 4,361,580 | 11/1982 | Peck et al. | 424/317 |
| 4,379,792 | 4/1983 | Blaine | 424/317 |

OTHER PUBLICATIONS

Steven M. Podos et al., "Investigative Ophthalmology", vol. 15, No. 10, pp. 841 to 844 (1976).

*Primary Examiner*—Douglas W. Robinson
*Attorney, Agent, or Firm*—Armstrong, Nikaido, Marmelstein & Kubovcik

[57] ABSTRACT

An anti-inflammatory ophthalmic solution containing (A) 2-(2-fluoro-4-biphenylyl)propionic acid or its ophthalmologically acceptable salt and (B) β-cyclodextrin or γ-cyclodextrin. The ophthalmic solution makes easy operations conducted for diseases in ophthalmic region, and is useful for early recovery or reduction of inflammation by pre- and post-operative topical instillation thereof or by intraocular perfusion with a perfusate to which the ophthalmic solution is added, or for treatment of inflammatory eye diseases.

5 Claims, 18 Drawing Figures

FIG.6-A    FIG.6-B    FIG.6-C    FIG.6-D
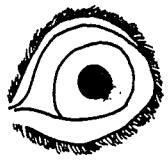   
FIG.7-A    FIG.7-B    FIG.7-C    FIG.7-D
   
FIG.8-A    FIG.8-B    FIG.8-C    FIG.8-D
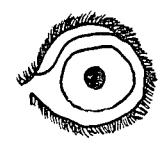   

ANTI-INFLAMMATORY OPHTHALMIC SOLUTION AND PROCESS FOR PREPARING THE SAME

BACKGROUND OF THE INVENTION

The present invention relates to a novel anti-inflammatory ophthalmic solution and the process for preparing the same, and more particularly to an anti-inflammatory ophthalmic solution containing 2-(2-fluoro-4-biphenylyl)propionic acid (hereinafter referred to as "FP") or its ophthalmologically acceptable salt and β-cyclodextrin (hereinafter referred to as "β-CD") or γ-cyclodextrin (hereinafter referred to as "γ-CD") which makes easy operations conducted for diseases in ophthalmic region, and is useful for early recovery or reduction of inflammation by pre- and post-operative topical instillation thereof or by intraocular perfusion with a perfusate to which the instant ophthalmic solution is added, or for treatment of inflammatory eye diseases.

When trauma is inflicted on the local of the eye in human by operation of anterior portion of the eye, such as operation of strabismus, cataract or glaucoma, prostaglandins (hereinafter referred to as "PGs") are biosynthetically produced and liberated from ocular tissue. It is also known that PGs are liberated in large quantities not only by such a mechanical irritation, but also in aqueous humor of the anterior chamber in the eye with a certain kind of uveitis such as Behçet's disease or at the time of glaucomatocyclitic crisis.

On the other hand, it is made clear that the PGs so liberated cause miosis and postoperative inflammation or elevate the intraocular pressure. For this reason, operation of soft cataract, etc. is made after sufficient mydriasis with atropine, etc., but miosis occurs during the operation and it makes the operation difficult. Therefore, there has been attempted oral administration of aspirin or indomethacin which is a nonsteroidal anti-inflammatory agent having an inhibitory effect on biosynthesis of PGs, for the purpose of inhibiting the biosynthesis of PGs which cause such symptoms, making operation easy and reducing complication and inflammation after the operation. However, in case of oral administration of these agents, they must be administered in large amounts for exhibiting their effect, since the amount of migration thereof to the local of the eye is small. On the other hand, administration of aspirin or indomethacin in large amounts accompanies a side effect such as digestive trouble, and is not clinically adoptable.

In order to migrate a drug in as large amount as possible without side effect, direct topical installation to the eye ball or injection to conjunctiva bulbi may be conducted. With respect to the former means, there has been attempted the use of indomethacin in the form of oil preparation, but the stability of the preparation is poor and the feeling in use is bad. Thus the preparation is not useful. With respect to the latter means, it is known that subconjuctival injection of polyphloretin phosphate as an inhibitor of PGs synthesis to a patient in glaucomatocyclitic crisis has an effect of decreasing the intraocular pressure, but it cannot also be habitually, clinically used, because it causes pain to a patient and eye pain or smart feeling is strong.

A nonsteroidal anti-inflammatory agent, FP, developed by S. S. Adams et al has the following structural formula and is a phenylacetic acid derivative as well as ibufenac and ibuprofen and has anti-inflammatory, analgesic and antipyretic effects:

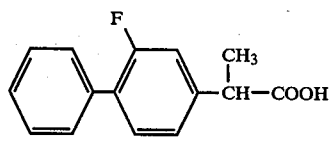

The anti-inflammatory effect of FP administered orally in animals is 14 times the inhibitory effect of indomethacin and 250 times the inhibitory effect of aspirin on carrageenan-induced edema in the pad of hind foot of rat. Also, the inhibitory effect of FP on biosynthesis of PGs from arachidonic acid in lung homogenate of guinea pig is 10 times that of indomethacin and 2,280 times that of aspirin.

Like this, FP has a strong inhibitory effect against quinine or PGs system, and the effect is also proportioned to the strength of the anti-inflammatory action. The effect is the strongest among known nonsteroidal anti-inflammatory agents. Also, strong effects are seen on the inflammatory pain and pyrexia accompanying therewith, and it has been considered that these effects are also largely based on the inhibition of PGs biosynthesis. In addition, FP has also an effect of stabilizing vital membrane, an effect of activating ATPase and an effect of inhibiting the liberation of leucocytes and proteins. Although the combination of the above-mentioned effects probably exerts the anti-inflammatory, analgesic and antipyretic actions, it has been considered that these actions are mainly based on the inhibitory effect on the PGs biosynthesis.

Steven M. Podos et al lately carried out a comparative study of the inhibitory effect of 14 nonsteroidal anti-inflammatory agents on the intraocular pressure elevation and aqueous humor protein increase by biosynthesis of PGs from arachidonic acid in rabbits, and reported that suspenions of indoxole (added with polysorbate), meclofenamic acid, indomethacin and clonixin, including an aqueous solution of FP, exhibited particularly strong inhibitory effects [cf. Invest. Ophthalmol., 15(10), 841 to 844(1976)]. However, it cannot be said that they are preparations completed as an ophthalmic solution or suspension, and they are not clinically usable and are not put to practical use.

It is an object of the present invention to prepare surely a safer opthalmic solution by using FP having a strong inhibitory effect on the PGs biosynthesis, in other words, to provide an ophthalmic solution which is effective even in a lower concentration of FP and can be used in a higher concentration of FP by making FP, which is usually of limited solubility, soluble in a high concentration, and does not show any local irritation and is stable for a long term.

Another object of the invention is to provide a process of preparing the above-mentioned ophthalmic solution.

These and other objects of the present invention will become apparent from the description hereinafter.

SUMMARY OF THE INVENTION

It has now been found that the above-mentioned objects of the present invention can be attained by using FP or its ophthalmologically acceptable salt in combination with β-CD or γ-CD.

The present invention has been accomplished on the basis of finding of entirely novel and surprising knowledges as follows: Although the irritation of FP to the human eye usually is enhanced when the concentration of FP is above 0.2% and the induction of a side effect such as keratohelcosis or chemosis other than the pharmacological effect is feared, the irritation of FP to the human eye is remarkably reduced under the coexistence with β-DC or γ-CD and no side effect occurs. The anti-inflammatory effect of FP depends on the intraocular concentration of FP and the concentration is remarkably increased under the coexistence with β-CD or γ-CD and the effect of FP is exhibited when the concentration of FP in the ophthalmic solution is not only high but also low. Under the coexistence with β-CD or γ-CD, the solubility of FP in a high concentration can be attained and the decrement of the above-mentioned irritation can be attained even by the use of FP in a high concentration. Moreover, an ophthalmic solution containing FP stable for a long term is obtained by coexisting FP with β-CD or γ-CD.

Accordingly, the ophthalmic solution of the present invention has an enlarged range of administration manner including frequent installation and applicability in a high concentration due to the fact that it is a non-irritative preparation and it can contain FP in dissolved state in a high concentration. The ophthalmic solution of the present invention effectively shows the inhibitory effect on intraocular PGs biosynthesis even in a low concentration of FP, and moreover, it shows more remarkably the inhibitory effect on intraocular PGs biosynthesis and enhances mydriasis effect of atropine in a high concentration of FP. Consequently, in ophthalmic operation such as operation for cataract, glaucoma, retinal detachment, vitrectomy or strabismus, it shows the excellent effect on maintenance of mydriasis, anti-inflammation or postoperative treatment. Moreover it effectively shows the treatment effect on symptoms of general ophthalmic diseases concerned with Pgs, for example, intrinsic uveitis such as Beçhet's disease. As mentioned above, the ophthalmic solution of the present invention is a very excellent ophthalmic solution which has no side effect such as eye irritation, is stable for a long term and is able to exert sufficiently the excellent pharmacological effect of FP.

BRIEF DESCRIPTION OF THE DRAWINGS

FIGS. 6-A, 6-B, 6-C and 6-D are figures showing state of rabbit eyes upon topical installation of Control and the ophthalmic solutions of Run Nos. 1, 4 and 12, 3 hours before the first paracentesis, respectively.

FIGS. 7-A, 7-B, 7-C and 7-D are figures showing state of rabbit eyes immediately before the first paracentesis after topical instillation of atropine, corresponding to FIGS. 6-A, 6-B, 6-C and 6-D, respectively.

FIGS. 8-A, 8-B, 8-C and 8-D are figures showing state of rabbit eyes immediately before the second paracentesis, corresponding to FIGS. 6-A, 6-B, 6-C and 6-D, respectively.

DETAILED DESCRIPTION

Figure 1:
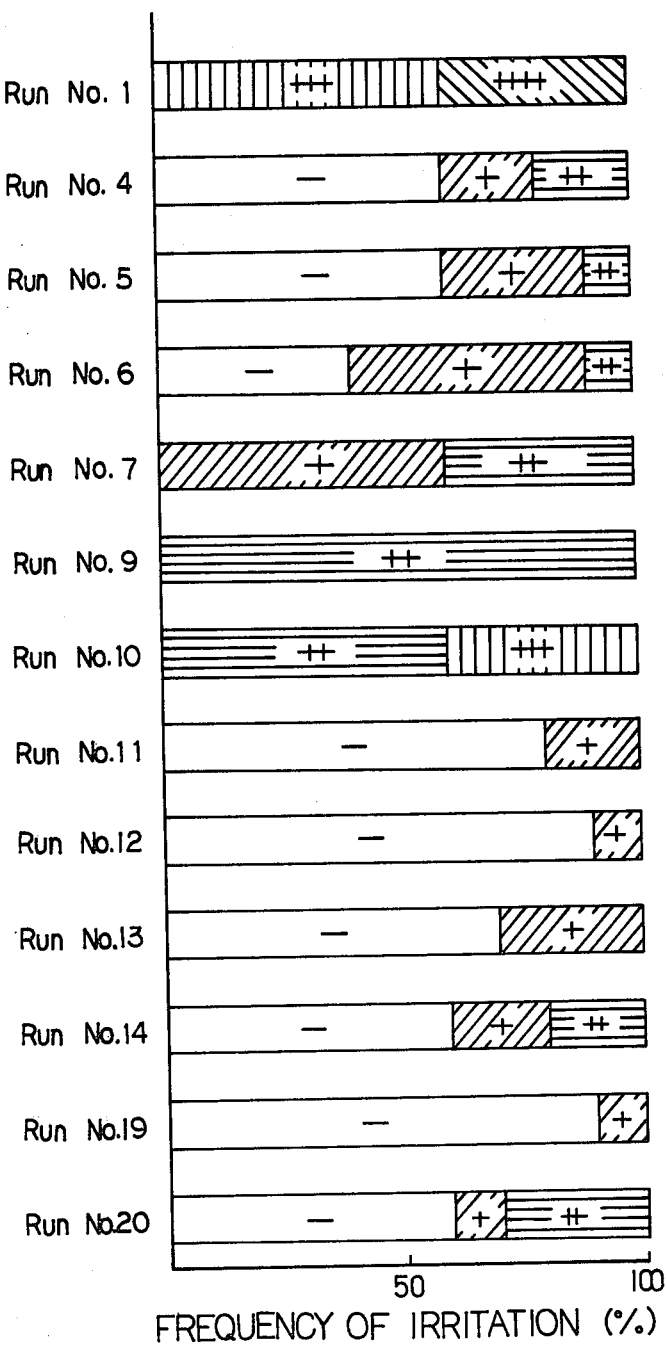
FIG. 1 is a graph showing frequency of irritation upon topical installation of the ophthalmic solutions of Run Nos. 1, 4, 5, to 7, 9 to 14, 19 and 20 to human eyes.

When FP and β-CD or γ-CD coexist in an aqueous medium, e.g. water, they usually form an inclusion complex. In the ophthalmic solution of the present invention, it is not necessary clear whether FP and β-CD or γ-CD must exist in a state of inclusion complex, but in any case, the desired effect is exhibited when FP coexists with β-CD or γ-CD. From this point of view, FP and β-CD or γ-CD may be added in various manners as mentioned hereinafter.

The ophthalmic solution of the present invention is prepared (1) (hereinafter referred to as "Method 1") by adding and dissolving FP or its ophthalmologically acceptable salt (hereinafter referred to as "the component (A)") and β-CD or γ-CD (hereinafter referred to as "the component (B)") to an aqueous medium, preferably further adding a viscosity-inducing agent and maintaining isotonicity by adjusting pH with a buffer agent, (2) (hereinafter referred to as "Method 2") by preparing in the same manner as in Method 1 except for adding and dissolving an inclusion complex of the component (A) with the component (B) to the aqueous medium, or (3) (hereinafter referred to as "Method 3") by preparing in the same manner as in Method 1 except for adding and dissolving the component (A), the component (B) and the above-mentioned inclusion complex to the aqueous medium. Method 1 is preferable from a preparative and economical point of view.

The component (A) used in the ophthalmic solution of the present invention may be any of the free acids of dl-, d- and l-isomers of FP and the salts thereof such as sodium, potassium, ammonium salts and amine addition salts.

It is preferable that the concentration of the component (A) is from 0.001 to 2 w/v %, more preferably from 0.005 to 1 w/v %. When the concentration of the component (A) is less than the above range, the inhibitory effect on the PGs biosynthesis is not remarkable.

In the above-mentioned Method 1, it is preferable that the molar ratio of the component (A) to the component (B) to be used is in the range of 1:0.5 to 1:2.5, especially in the range of 1:1 to 1:2.0 and this range is preferable to increase the intraocular penetration of the component (A). It is preferable that the molar ratio of the component (A) to the component (B) contained in the inclusion complex used in the above-mentioned Method 2 is in the range of 1:0.5 to 1:2.5, more preferably in the range of 1:1 to 1:2.0. And in the above-mentioned Method 3, it is preferable that the molar ratio of the component (A) to the component (B) to be used in the range of 1:0.5 to 1:2.5, more preferably 1:1 to 1:2.0 and that the component (A) and the component (B) contained in the inclusion complex to be used is in the molar ratio of 1:0.5 to 1:2.5, more preferably 1:1 to 1:2.0.

The viscosity-inducing agent has an effect of accelerating the permeability of the component (A) through the cornea and thus increasing the intraocular penetration thereof as a result of giving viscosity to the ophthalmic solution so as to increase the affinity of the component (A) to the cornea and the period that the component (A) stays in the eye. Examples of the viscosity-inducing agent are polyvinyl alcohol, methyl cellulose, carboxymethyl cellulose, hydroxyethyl cellulose, hydroxypropyl methyl cellulose, sodium salt of chondroitin sulfuric acid and polyvinylpyrrolidone. These compounds may be employed alone or in admixture thereof. Hydroxyethyl cellulose or hydroxypropyl methyl cellulose is preferred because of uniform quality and good solubility.

It is preferable that the viscosity-inducing agent is used in such an amount that the resulting solution has a relative viscosity of 2 to 30 cP., especially 2 to 20 cP.

The ophthalmic solution of the present invention is adjusted to pH 5.0 to 8.0, preferably pH 6.0 to 7.5. In this pH range, an isotonic solution in which FP is dissolved in a high concentration is preferably prepared and the intraocular penetration of the component (A) increases. When the pH value is higher than the above range, the intraocular penetration of the component (A) is lowered, and when the pH value is lower than the above range, the solubility of the component (A) is lowered.

As a buffer agent for pH adjustment, any of those which are ophthalmologically acceptable may be employed without particular limitation. Preferable examples are, for instance, phosphates, borates, bicarbonates, acetates and tris-amine salts. Among them, a combination of sodium dihydrogenphosphate and disodium hydrogenphosphate is especially preferred.

In addition to the above-mentioned components, the ophthalmic solution of the present invention may be incorporated with usual preservatives such as chlorobutanol, methyl p-hydroxybenzoate, propyl p-hydroxybenzoate, benzyl alcohol, benzalkonium chloride, benzethonium chloride, disodium edetate and sodium dehydroacetate and usual additives such as sodium chloride, potassium chloride and boric acid.

The ophthalmic solution of the present invention is prepared according to the above-mentioned Method 1, Method 2 or Method 3, and more concretely, for example, by adding and dissolving (1) the component (A) and the component (B), (2) the inclusion complex of the component (A) with the component (B) or (3) the component (A), the component (B) and the inclusion complex thereof in an aqueous solution of a buffer agent, and if necessary, further adding and dissolving a viscosity-inducing agent and a preservative, adding water to the resulting solution to adjust to a desired concentration and filtering to sterilize. A sterile, purified water is usually employed as a medium.

The ophthalmic solution of the present invention is explained by means of Examples. These Examples are intended to illustrate the invention and not be construed to limit the scope of the invention. It is to be understood that various changes and modifications may be made in the invention without departing from the spirit and scope thereof.

EXAMPLE 1

Ophthalmic solutions were prepared according to prescriptions shown in Table 1. The ophthalmic solution of Run. No. 1 was a preparation of FP-only formula prepared as a Comparative Example.

TABLE 1

| Components (g.) | Run No. 1 | 2 | 3 | 4 | 5 | 6 | 7 | 8 | 9 | 10 |
|---|---|---|---|---|---|---|---|---|---|---|
| FP | 0.1 | 0.1 | 0.1 | 0.1 | 0.1 | 0.2 | 0.5 | 0.5 | 1.0 | 1.3 |
| $\beta$-CD | — | 0.675 | 0.545 | 0.465 | 0.465 | 0.930 | 2.325 | 1.859 | 4.65 | 6.045 |
| Inclusion complex of FP with $\gamma$-CD { FP / $\gamma$-CD } | — | — | — | — | — | — | — | — | — | — |
| Disodium hydrogenphosphate | 2.50 | 2.50 | 2.50 | 2.50 | 2.50 | 3.30 | 3.40 | 3.40 | 3.50 | 3.60 |
| Sodium dihydrogenphosphate | 0.15 | 0.15 | 0.15 | 0.15 | 0.15 | 0.335 | 0.20 | 0.20 | 0.18 | 0.15 |
| Sodium chloride | 0.24 | 0.24 | 0.24 | 0.24 | 0.24 | — | — | — | — | — |
| Chlorobutanol | 0.30 | 0.30 | 0.30 | 0.30 | 0.30 | — | — | — | — | — |
| Benzalkonium chloride | — | — | — | — | — | 0.009 | 0.009 | — | — | — |
| Methyl p-hydroxybenzoate | — | — | — | — | — | 0.02 | — | — | — | — |
| Propyl p-hydroxybenzoate | — | — | — | — | — | — | — | — | — | — |
| Sodium dehydroacetate | — | — | — | — | — | — | — | 0.08 | 0.08 | 0.08 |
| Disodium edetate | — | — | — | — | — | — | 0.02 | — | — | — |
| Hydroxypropyl methyl cellulose | — | — | 0.20 | 0.20 | — | 0.20 | 0.20 | 0.20 | 0.20 | 0.20 |
| Hydroxyethyl cellulose | — | — | — | — | — | — | — | — | — | — |
| Polyvinyl alcohol | — | — | — | — | — | — | — | — | — | — |
| Total volume (ml.) | 100 | 100 | 100 | 100 | 100 | 100 | 100 | 100 | 100 | 100 |
| Concentration of FP (w/v %) | 0.1 | 0.1 | 0.1 | 0.1 | 0.1 | 0.2 | 0.5 | 0.5 | 1.0 | 1.3 |
| FP : $\beta$-CD (or $\gamma$-CD) (molar ratio) | — | 1:1.45 | 1:1.17 | 1:1 | 1:1 | 1:1 | 1:1 | 1:0.8 | 1:1 | 1:1 |
| pH | 7.20 | 7.20 | 7.20 | 7.20 | 7.20 | 7.21 | 7.19 | 7.18 | 7.15 | 7.10 |
| Osmotic pressure (mOs.) | 300 | 292 | 302 | 300 | 299 | 297 | 305 | 298 | 302 | 310 |
| Viscosity (cP.) | 1.05 | — | — | 5.72 | — | — | — | — | — | — |

| Components (g.) | Run No. 11 | 12 | 13 | 14 | 15 | 16 | 17 | 18 | 19 | 20 |
|---|---|---|---|---|---|---|---|---|---|---|
| FP | 0.1 | 0.1 | 0.15 | 0.2 | — | — | — | — | — | — |
| $\beta$-CD | 0.735 | 0.735 | 1.20 | 1.68 | — | — | — | — | — | — |
| Inclusion complex of FP with $\gamma$-CD { FP / $\gamma$-CD } | — | — | — | — | 0.1 / 0.531 | 0.2 / 1.062 | 0.5 / 2.665 | 1.0 / 5.309 | 0.1 / 1.195 | 0.2 / 1.70 |
| Disodium hydrogenphosphate | 2.40 | 2.40 | 2.40 | 2.50 | 3.20 | 3.30 | 3.40 | 3.55 | 2.40 | 2.50 |
| Sodium dihydrogenphosphate | 0.61 | 0.61 | 0.58 | 0.58 | 0.36 | 0.335 | 0.20 | 0.18 | 0.61 | 0.58 |
| Sodium chloride | — | — | — | — | — | — | — | — | — | — |
| Chlorobutanol | 0.4 | 0.4 | 0.5 | 0.4 | — | — | — | — | 0.4 | 0.5 |
| Benzalkonium chloride | — | — | — | — | — | — | — | — | — | — |

TABLE 1-continued

| | | | | | | | | | | |
|---|---|---|---|---|---|---|---|---|---|---|
| Methyl p-hydroxybenzoate | — | — | — | — | 0.036 | 0.036 | 0.036 | 0.036 | — | — |
| Propyl p-hydroxybenzoate | — | — | — | — | 0.019 | 0.019 | 0.019 | 0.019 | — | — |
| Sodium dehydroacetate | — | — | — | — | — | — | — | — | 0.1 | — |
| Disodium edetate | — | — | — | — | — | — | — | — | — | — |
| Hydroxypropyl methyl cellulose | — | — | — | — | 0.30 | 0.30 | 0.30 | 0.30 | — | — |
| Hydroxyethyl cellulose | — | 0.2 | 0.1 | 0.2 | — | — | — | — | 0.2 | — |
| Polyvinyl alcohol | — | — | 1.5 | — | — | — | — | — | — | 1.5 |
| Total volume (ml.) | 100 | 100 | 100 | 100 | 100 | 100 | 100 | 100 | 100 | 100 |
| Concentration of FP (w/v %) | 0.1 | 0.1 | 0.15 | 0.2 | 0.1 | 0.2 | 0.5 | 1.0 | 0.1 | 0.2 |
| FP : β-CD (or γ-CD) (molar ratio) | 1:1.58 | 1:1.58 | 1:1.72 | 1:1.8 | 1:1 | 1:1 | 1:1 | 1:1 | 1:2.25 | 1:1.60 |
| pH | 6.83 | 6.81 | 6.80 | 6.77 | 7.19 | 7.20 | 7.20 | 7.20 | 6.82 | 6.80 |
| Osmotic pressure (mOs.) | 297 | 298 | 317 | 304 | 298 | 300 | 291 | 297 | 302 | 309 |
| Viscosity (cP.) | 1.09 | 4.65 | 4.64 | 4.55 | — | — | — | — | 4.71 | 3.22 |

The ophthalmic solutions were prepared in the following manners:

(1) [The ophthalmic solutions of Run Nos. 1, 2, 5 and 11]

Those ophthalmic solutions were prepared by dissolving chlorobutanol in a sterile, purified water, then dissolving therein sodium dihydrogenphosphate and disodium hydrogenphosphate, and further FP and β-CD (as for Run No. 1, FP only), adding NaCl to adjust the solution to isotonicity, and after adding a sterile, purified water to the solution to adjust the total volume, sterilizing the resultant through a filter.

(2) [The ophthalmic solutions of Run Nos. 3, 4 and 6 to 10]

Those ophthalmic solutions were prepared by dissolving hydroxypropyl methyl cellulose (4000), disodium hydrogenphosphate and sodium dihydrogenphosphate in a sterile, purified water, dissolving FP and β-CD in the solution, dissolving one or two kinds of preservants selected from chlorobutanol, benzalkonium chloride, methyl p-hydroxybenzoate, sodium dehydroacetate and disodium edetate in the solution, and after adding a sterile, purified water to the solution to adjust the total volume, sterilizing the resultant through a filter.

(3) [The ophthalmic solutions of Run Nos. 15 to 18]

Those ophthalmic solutions were prepared by dissolving hydroxypropyl methyl cellulose (4000), methyl p-hydroxybenzoate and propyl p-hydroxybenzoate in a sterile, purified water, adding and dissolving disodium hydrogenphosphate and sodium dihydrogenphosphate, then dissolving the inclusion complex of FP with γ-CD in the solution, and after adding a sterile, purified water to the solution to adjust the total volume, sterilizing the resultant through a filter.

(4) [The ophthalmic solutions of Run Nos. 12, 13 and 14]

Those ophthalmic solutions were prepared by dissolving one or two kinds of viscosity-inducing agents selected from hydroxypropyl methyl cellulose (4000), hydroxyethyl cellulose (6300) and polyvinyl alcohol, further disodium hydrogenphosphate and sodium dihydrogenphosphate in a sterile, purified water, adding and dissolving FP and β-CD, further chlorobutanol in the solution, and after adding a sterile, purified water to the solution to adjust the total volume, sterilizing the resultant through a filter.

(5) [The ophthalmic solutions of Run Nos. 19 and 20]

Those ophthalmic solutions were prepared by dissolving hydroxyethyl cellulose (6300) in a sterile, purified water, adding and dissolving disodium hydrogenphosphate and sodium dihydrogenphosphate in the solution, dissolving chlorobutanol alone or chlorobutanol and sodium dehydroacetate in the solution, then dissolving the inclusion complex of FP with γ-CD, and the residual amount of γ-CD, and after adding a sterile, purified water to the solution to adjust the total volume, sterilizing the resultant through a filter.

An ophthalmic solution other than the above-mentioned solutions was prepared in the same manner as in Run No. 6 except that 0.1 g of FP out of the total amount of FP used (0.2 g.) and 0.465 g. of β-CD out of the total amount of β-CD used (0.930 g.) were added in the form of FP per se and in the form of β-CD per se, respectively, and the residual amounts of FP and β-CD were added in the form of an inclusion complex thereof.

The ophthalmic solutions of Run Nos. 2 to 20 placed in a plastic container for ophthalmic solution did not show any change as the ophthalmic solution of Run No. 1 did not, even in storage for one month in a sunlight box [40° C., relative humidity 80% (or 50° C., relative humidity 50%), continuous irradiation of artificial sunlight at 6,000 luxes by means of a sunlight lamp every other day].

The obtained ophthalmic solutions were then subjected to the following tests.

TEST EXAMPLE 1

[Irritation to the human eye]

A drop (approximately 40 μl.) of each of the ophthalmic solutions of Run Nos. 1, 4 to 7, 9 to 14, 19 and 20 was instilled to 10 normal adult men, and the degree of irritation was observed. The results are shown in Table 2 and FIG. 1. The frequency of irritation in Table 2 and FIG. 1 was estimated according to the following criteria:

TABLE 2

| | FIG. 1 | |
|---|---|---|
| 0 | (−): | non-irritated and non-unpleasant |
| 1 | (+): | slightly irritated |
| 2 to 3 | (++): | irritated |
| 4 | (+++): | strongly irritated |
| 5 | (++++): | strongly, intolerably irritated |

| | Ophthalmic solution Run No. | | | | | | | | | | |
|---|---|---|---|---|---|---|---|---|---|---|---|
| Man | 1 | 4 | 5 | 6 | 7 | 9 | 10 | 11 | 12 | 13 | 14 | 19 | 20 |
| 1 | 5 | 0 | 1 | 0 | 1 | 2 | 4 | 0 | 0 | 0 | 0 | 0 | 0 |
| 2 | 4 | 1 | 0 | 2 | 2 | 3 | 3 | 0 | 0 | 1 | 2 | 1 | 3 |
| 3 | 4 | 0 | 1 | 1 | 1 | 2 | 4 | 0 | 1 | 0 | 1 | 0 | 3 |
| 4 | 5 | 2 | 0 | 0 | 1 | 2 | 3 | 1 | 0 | 0 | 0 | 0 | 1 |
| 5 | 5 | 0 | 0 | 1 | 2 | 3 | 4 | 0 | 0 | 1 | 0 | 0 | 0 |
| 6 | 5 | 0 | 0 | 1 | 1 | 3 | 3 | 0 | 0 | 0 | 0 | 0 | 0 |
| 7 | 4 | 1 | 1 | 1 | 2 | 3 | 3 | 0 | 0 | 0 | 1 | 0 | 0 |
| 8 | 4 | 0 | 0 | 0 | 2 | 2 | 3 | 0 | 0 | 0 | 0 | 0 | 0 |
| 8 | 4 | 0 | 0 | 0 | 2 | 2 | 3 | 0 | 0 | 0 | 0 | 0 | 0 |
| 9 | 4 | 2 | 0 | 1 | 1 | 3 | 4 | 1 | 0 | 1 | 3 | 0 | 2 |

TABLE 2-continued

FIG. 1

| | | |
|---|---|---|
| 0 | (−): | non-irritated and non-unpleasant |
| 1 | (+): | slightly irritated |
| 2 to 3 | (++): | irritated |
| 4 | (+++): | strongly irritated |
| 5 | (++++): | strongly, intolerably irritated |

| Man | Ophthalmic solution Run No. | | | | | | | | | | | | |
|---|---|---|---|---|---|---|---|---|---|---|---|---|---|
| | 1 | 4 | 5 | 6 | 7 | 9 | 10 | 11 | 12 | 13 | 14 | 19 | 20 |
| 10 | 4 | 0 | 2 | 0 | 1 | 3 | 3 | 0 | 0 | 0 | 0 | 0 | 0 |
| Sum | 44 | 6 | 5 | 7 | 16 | 23 | 34 | 2 | 1 | 3 | 7 | 1 | 9 |
| Mean | 4.4 | 0.6 | 0.5 | 0.7 | 1.6 | 2.3 | 3.4 | 0.2 | 0.1 | 0.3 | 0.7 | 0.1 | 0.9 |

As shown in Table 2 and FIG. 1, a significant difference of irritation was found between the preparation of FP-only formula (Run No. 1) and the preparations of the present invention containing FP and β-CD (Run Nos. 4 to 7, 9 to 14) or containing FP and γ-CD (Run Nos. 19 and 20) and it was proved that the ophthalmic solutions of the present invention had no irritation.

TEST EXAMPLE 2

(Inhibitory effect on aqueous humor protein increase by paracentesis)

To one eye of rabbits was instilled 4 times 50 μl. of each of the ophthalmic solutions of Run Nos. 4, 6, 7, 9 and 12 to 14 (the preparations containing FP and β-CD) and Run No. 1 (the FP-only preparation) 3, 2, 1 and 0.5 hour before paracentesis. To the other eye was instilled each of corresponding solutions not containing the effective components (FP and β-CD) as a control in the same manner as above.

The rabbits were fixed, and the aqueous humor of the anterior chamber was taken under anesthetic condition by employing a needle of injection (primary aqueous humor) and was taken again 1.5 hours after the first collection (secondary aqueous humor). The concentration of protein in each aqueous humor was measured according to the method of Lowry et al. The results are shown in FIG. 2.

Figure 2:
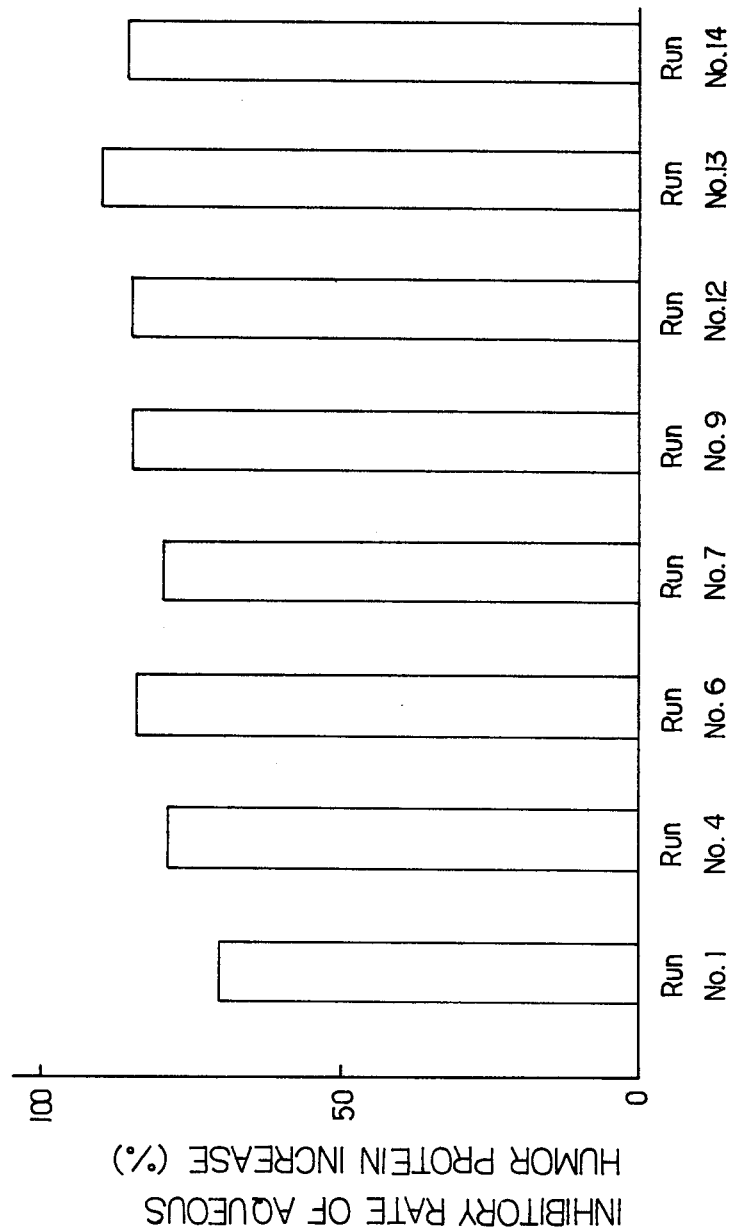
FIG. 2 is a graph showing inhibitory rate of aqueous humor protein increase upon topical installation of the ophthalmic solutions of Run Nos. 1, 4, 6, 7, 9 and 12 to 14 to rabbit eyes.

From FIG. 2, it is understood that the preparations containing FP and β-CD of the present invention (Run Nos. 4, 6, 7, 9 and 12 to 14) exhibit an inhibitory effect on intraocular protein biosynthesis equal to or better than that of the FP-only preparation (Run No. 1).

TEST EXAMPLE 3

(Effect on permeability of blood-aqueous barrier after operation of cataract)

The method of determining the permeability of iris vessel, the rate of aqueous humor induction and the permeability of endothelium camerae anterioris in the human eye by measuring the concentrations of fluorescein in anterior chamber, plasma and the middle of cornea after oral administration of fluorescein and applying the obtained data to a theoretical equation has been developed by Mishima, Araie et al. (M. Araie, M. Sawa, S. Nagataki, and S. Mishima, "Aqueous humor dynamics in man as studied by oral fluorescein", Jpn. J. Ophthalmol., 24, P346 to 362, 1980).

That is, the method has been established of calculating iris transfer coefficient (hereinafter referred to as "K'd·pa") and the coefficient of aqueous humor flow (hereinafter referred to as "K'fa") separately in tested eyes by orally administering an aqueous solution of fluorescein and applying the measured change of the concentrations of fluorescein in anterior chamber and plasma to the Kinsey-Palm equation (V. E. Kinsey, and E. Palm, "Posterior and anterior chamber aqueous formation", Arch ophthalmol., 53, P330 to 344, 1955) using the least-squares method.

The permeability of blood-aqueous barrier has a close relationship with the K'd·pa value. Therefore, using the K'd·pa value as a quantitative index of the permeability of blood-aqueous barrier, the effect of instillation of FP on change of the permeability of blood-aqueous barrier after operation of cataract was studied.

(i) Instillation

Patients of cataract were classified into following 4 groups according to whether or not they were subjected to instillation of FP in addition to conventional instillation, and to the kinds of the FP-containing ophthalmic solutions used.

Group No. 1 (Control)

This group comprised 13 patients (the mean age: 64±9 years old) and was treated by conventional postoperative instillation. That is, no preoperative instillation was applied, and after operation, a 1 w/v % atropine solution was administered once a day, a 0.1 w/v % betamethasone solution was administered 4 times a day and an antibiotics was administered 4 times a day.

Group Nos. 2 to 4

Each group comprised 7 patients (the mean age: 72±7 years old) and was treated by instillation of the ophthalmic solution containing 0.1 w/v % of FP in addition to the conventional instillation. The preparations of Run No. 1 (FP-only preparation) and Run Nos. 4 and 12 (preparations containing FP and β-CD) were used in Group Nos. 2, 3 and 4, respectively. Those FP-containing ophthalmic solutions were instilled 3, 2, 1 and 0.5 hour before operation and twice a day in the morning and in the evening after operation in addition to conventional instillation treatment.

(ii) Measurement of fluorescence

Six days after the operation, fluorescein in the form of a 10 w/v % aqueous solution of its sodium salt was administered orally in a dose of 5 mg./kg. to all the cases tested, and the fluorescence in anterior chamber of both eyes was measured at intervals of 1 hour with a fluorophotometer of slit lamp type. Moreover about 1 ml. of blood was taken at intervals of 1 hour and the concentration of fluorescein in the plasma thereof was measured.

(iii) Analysis method

Kinsey-Palm equation is modified as in the following Equation (I):

$$dC'a/dt = K'd \cdot pa \, (C'p - C'a) - K'fa C'a \qquad (I)$$

wherein C'a designates the apparent concentration of fluorescein in anterior chamber, C'p designates the total concentration of fluorescein in plasma, K'd·pa and K'fa designate the same as mentioned above.

C'a and C'p calculated from the measured values were applied to Equation (I) using the least squares method, and K'd·pa and K'fa in postoperative eyes were calculated.

Figure 3:
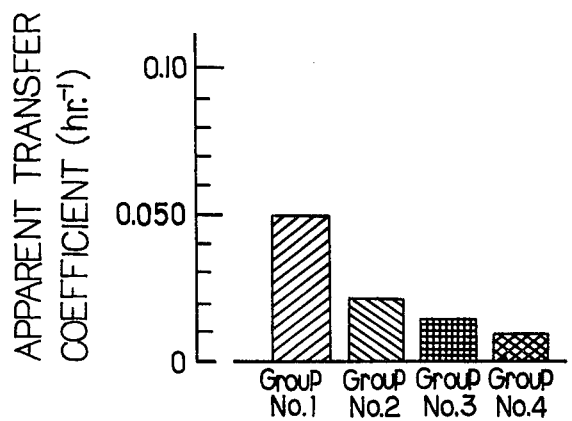
FIG. 3 is a graph showing iris transfer coefficient by diffusion ("K'd·pa") upon use of the ophthalmic solutions of Run Nos. 1, 4 and 12 at the time of operation for cataract.
Figure 4:
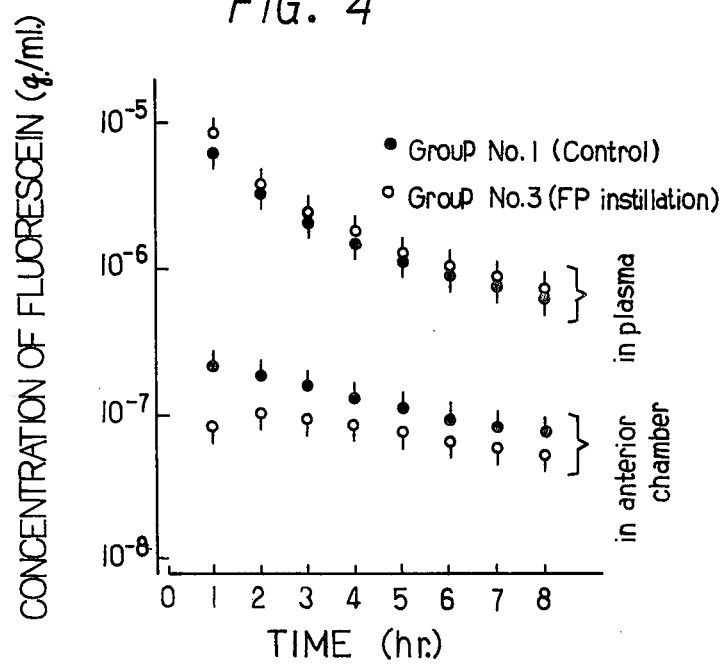
FIG. 4 is a graph showing concentration of fluorescein in plasma and anterior chamber under the same condition as in FIG. 3.

The results are shown in Table 3, FIGS. 3 and 4. FIG. 3 shows the iris transfer coefficient and FIG. 4 shows the concentrations of fluorescein in plasma and anterior chamber. In Table 3, there are also shown the results of the test by M. Araie et al. wherein the same test as mentioned above was carried out using an oily ophthalmic solution containing 0.5% of indomethacin (hereinafter referred to as "IM") (see M. Araie et al., "Indomethacin instillation and permeability of blood-aqueous barrier after operation of cataract: quantitative analysis by fluorophotometry", Acta Soc. Ophthalmol. Jpn. 85(9), P1279 to 1286, 1981).

TABLE 3

| Instillation | Number of patient | $K'd \cdot pa\ (hr.^{-1})$ (Mean ± SD) |
|---|---|---|
| FP instillation | | |
| Group No. 1 (Control) | 13 | 0.050 ± 0.055 |
| Group No. 2 (Run No. 1) | 7 | 0.024 ± 0.014 |
| Group No. 3 (Run No. 4) | 7 | 0.020 ± 0.012 |
| Group No. 4 (Run No. 12) | 7 | 0.016 ± 0.007 |
| IM Instillation | | |
| Group No. 1 (Control) | 13 | 0.050 ± 0.055 |
| Group No. 5 (oily ophthalmic solution of IM) | 14 | 0.017 ± 0.015 |

As shown in Table 3, there was observed a significant difference between each K'd·pa value of Group No. 3, Group No. 4 and Group No. 5 and the K'd·pa value of Control according to the U-test of Mann Whitney ($P < 0.05$).

The usability of IM instillation has been already estimated highly, since the inhibition on increase of permeability of blood-aqueous barrier after operation by adding IM instillation is about 3 times that in case of adding no IM instillation.

From the above-mentioned facts, it was confirmed that the FP-containing ophthalmic solution of the present invention had a more excellent inhibitory effect on increase of permeability of blood-aqueous barrier than the conventional FP-containing ophthalmic solution and had a usability equal to or better than the oily ophthalmic solution containing IM.

TEST EXAMPLE 4

(Mydriasis effect)

Even if a preoperative mydriasis treatment is performed, miosis occurs during the operation and it makes the operation difficult. This antiantropine-like miosis is considered to be induced by PGs. Therefore tests with respect to the mydriasis effect were made using the ophthalmic solution of the present invention, since sufficient mydriasis effect would be expected by the administration of the ophthalmic solution of the present invention which inhibits the PGs biosynthesis.

(i) Mydriasis effect of atropine

Mydriasis induced by atropine instillation was first observed, assuming that a mydriasis treatment is usually performed prior to operation.

The test was performed using 5 rabbits, and a drop (40 μl.) of a 1 w/v % solution of atropine sulfate in physiological salt solution was instilled to the right eye of the rabbits, and the change of status of the eye with lapse of time was observed by the photographic determination of pupillary diameter. The pupillary diameter difference [(the pupillary diameter at each time after instillation)—(the pupillary diameter before instillation)] and rate of mydriasis (%), which was calculated according to the following formula, were determined.

$$\text{Rate of mydriasis (\%)} = \frac{\left(\begin{array}{c}\text{Pupillary diameter}\\\text{at each time after}\\\text{instillation}\end{array}\right) - \left(\begin{array}{c}\text{Pupillary diameter}\\\text{before instillation}\end{array}\right)}{(\text{Pupillary diameter before instillation})} \times 100$$

Figure 5:
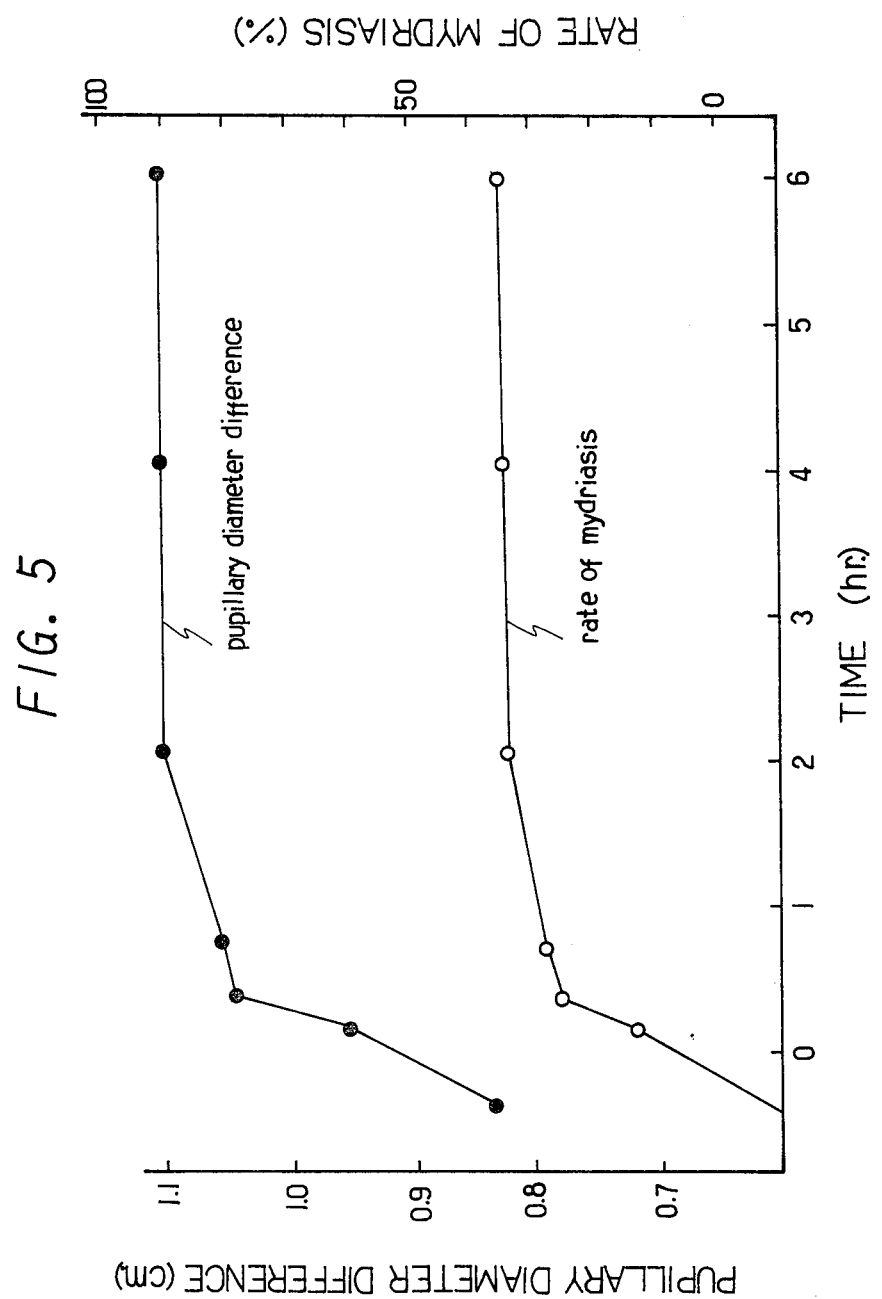
FIG. 5 is a graph showing pupillary diameter difference and rate of mydriasis upon topical instillation of atropine.

The results are shown in FIG. 5. The pupillary diameter difference and the rate of mydriasis in FIG. 5 are the mean values as to 5 rabbits.

As shown in FIG. 5, the pupillary diameter became to the maximum one hour after the instillation of atropine and no change in the maximum diameter was observed even after 6 hours from the instillation. Thus the mydriasis effect of atropine instillation was confirmed.

(2) Mydriasis effect of atropine at the time of inflammation

The following test was made so as to observe the continuity of the mydriasis effect of atropine at the time of inflammation, which would be expected to be an index of the inhibitory effect of the instillation of the instant ophthalmic solution on PGs biosynthesis.

Five rabbits were used as one group in the test. To the right eye of each rabbit of a group was instilled the instant preparation containing FP and β-CD (Run No. 4 or Run No. 12). To the right eye of each rabbit of another group was instilled the FP-only preparation (Run No. 1). To the left eye of each rabbit of the above two groups was instilled each of corresponding ophthalmic solutions containing no effective component. To both eyes of each rabbit of still another group was instilled each of corresponding solutions containing no effective component (Control). All solutions were instilled in an amount of a drop (about 40 μl.) 3 hours, 2 hours, 1 hour and 0.5 hour before operation. The states of the eyes of the rabbits when each of the solutions was instilled 3 hours before operation are shown in FIG. 6-A (Control), FIG. 6-B (Run No. 1), FIG. 6-C (Run No. 4) and FIG. 6-D (Run No. 12).

To both eyes of the rabbits was instilled a drop (approximately 40 μl.) of a 1 w/v % solution of atropine sulfate in physiological salt solution. After 1.5 hours from the atropine instillation, the first paracentesis was conducted. The states of the eyes of the rabbits immediately before the first paracentesis are shown in FIG. 7-A (Control), FIG. 7-B (Run No. 1), FIG. 7-C (Run No. 4) and FIG. 7-D (Run No. 12).

The second paracentesis was conducted after 1.5 hours from the first paracentesis. The states of the eyes of the rabbits immediately before the second paracentesis are shown in FIG. 8-A (Control), FIG. 8-B (Run No. 1), FIG. 8-C (Run No. 4) and FIG. 8-D (Run No. 12).

The rate of mydriasis of the eyes of the rabbits immediately before the second paracentesis was calculated in the same manner as mentioned above. The results are shown in Table 4.

TABLE 4

| Ophthalmic solution | Rate of mydriasis (%) |
|---|---|
| Run No. 1 | 37.60 |
| Run No. 4 | 43.61 |
| Run No. 12 | 46.18 |

TABLE 4-continued

| Ophthalmic solution | Rate of mydriasis (%) |
| --- | --- |
| Control | −17.5 |

As obvious from FIGS. 6-A, 6-B, 6-C, 6-D, FIGS. 7-A, 7-B, 7-C, 7-D, FIGS. 8-A, 8-B, 8-C, 8-D, and Table 4, it was proved that the mydriasis effect of atropine was continued by installtion of the instant preparation containing FP and β-CD as a manifestion of inhibitory effect on PGs biosynthesis and that the effect of the instant ophthalmic solution on the continuity was superior to that of the FP-only preparation (Run No. 1).

TEST EXAMPLE 5

(Effect of pH on intraocular permeation of FP)

(i) FP-only preparation

Ophthalmic solutions were prepared in the same manner as in above-mentioned Run No. 1 except that the amounts of sodium dihydrogenphosphate and disodium hydrogenphosphate were changed to adjust the pH values of the resulting solutions as shown in Table 5. To the eyes of rabbits was instilled 50 μl. of each ophthalmic solution, and the aqueous humor of the anterior chamber was taken after 2 hours from instillation and the concentration of FP in the aqueous humor was measured. The results are shown in Table 5.

TABLE 5

| Run No. | 21 | 22 | 23 | 24 | 25 |
| --- | --- | --- | --- | --- | --- |
| pH of solution | 5.33 | 6.20 | 6.76 | 7.73 | 8.05 |
| Concentration of FP in aqueous humor (μg./g.) | 1.33 | 1.16 | 1.00 | 0.75 | 0.60 |

(2) Preparation containing FP and β-CD

Ophthalmic solutions were prepared in the same manner as in Run No. 2 except that the pH values of the resulting solutions were adjusted as shown in Table 6 in the same manner as in the above (1). The obtained ophthalmic solutions were instilled to the eyes of the rabbits and the concentration of FP in the aqueous humor was measured in the same manner as in the above (1). The results are shown in Table 6.

TABLE 6

| Run No. | 26 | 27 | 28 | 29 | 30 |
| --- | --- | --- | --- | --- | --- |
| pH of solution | 5.36 | 6.20 | 6.78 | 7.70 | 8.10 |
| Concentration of FP in aqueous humor (μg./g.) | 1.78 | 1.48 | 1.12 | 0.83 | 0.66 |

From Table 5 and Table 6, it was observed that there was a correlation between the intraocular permeation of FP and the pH of the ophthalmic solution. In case of the preparations of the present invention containing FP and β-CD, the intraocular permeation of FP was remarkably improved, especially in a lower pH range, because the above-mentioned preparations had much lesser irritation than the FP-only preparation so that the amount of the preparation flowed out of eyes by wink was small.

TEST EXAMPLE 6

(Effect of viscosity-inducing agent on intraocular permeation of FP)

By employing each of the ophthalmic solutions of Run Nos. 4, 5, 11 and 12, the concentration of FP in the aqueous humor of the anterior chamber was measured in the same manner as in Test Example 5. The results are shown in FIG. 9.

Figure 9:
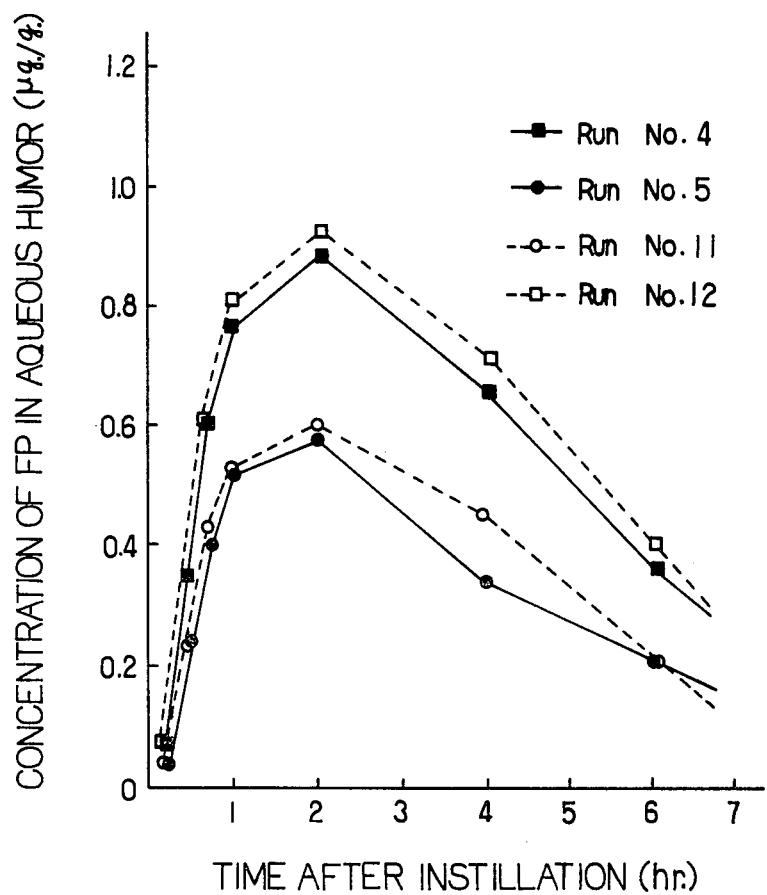
FIG. 9 is a graph showing the concentration of FP in aqueous humor upon topical instillation of the ophthalmic solutions of Run Nos. 4, 5, 11 and 12 to rabbit eyes, respectively.

From FIG. 9, it was observed that the intraocular permeation of FP in case of using the solution containing a viscosity-inducing agent (hydroxypropyl methyl cellulose or hydroxyethyl cellulose) was 1.5 times that in case of using the solution containing no viscosity-inducing agent.

The above results reveal that the ophthalmic solution of the present invention is non-irritative to exhibit a sufficient clinical effect and shows an excellent intraocular permeation of FP, and it has become apparent that the ophthalmic solution of the present invention can be applied to not only operations of eyes but also usual ophthalmic diseases and are usable within the range of FP concentration of 0.001 to 2 w/v % as a clinically useful ophthalmic solution.

What we claim is:

1. An anti-inflammatory ophthalmic solution comprising (A) an ophthalmologically anti-inflammatory effective amount of 2-(2-fluoro-4-biphenylyl)propionic acid or its ophthalmologically acceptable salt and (B) β-cyclodextrin or γ-cyclodextrin in an aqueous medium, the molar ratio of component (A) to component (B) being from 1:0.5 to 1:2.5.

2. The anti-inflammatory ophthalmic solution of claim 1, wherein the concentration of the component (A) is from 0.001 to 2 w/v %.

3. The anti-inflammatory ophthalmic solution of claim 1, which further contains an ophthalmologically acceptable viscosity-inducing agent in an amount such that the ophthalmic solution has a relative viscosity of from 2 to 30 cP.

4. The anti-inflammatory ophthalmic solution of claim 1, which is adjusted to pH 5.0 to 8.0 with a buffer agent.

5. The anti-inflammatory ophthalmic solution of claim 1 wherein component (A) and component (B) are present in the form of an inclusion complex.

* * * * *